(12) United States Patent
Kim et al.

(10) Patent No.: US 9,962,390 B2
(45) Date of Patent: May 8, 2018

(54) MOSAPRIDE SUSTAINED-RELEASE FORMULATION PROVIDING PHARMACOLOGICAL AND CLINICAL EFFECTS WITH ONCE-DAILY ADMINISTRATION

(71) Applicant: Korea United Pharm. Inc., Sejong-si (KR)

(72) Inventors: Byung Jin Kim, Sejong-si (KR); Youn Woong Choi, Gyeonggi-do (KR); Hee Yong Song, Sejong-si (KR); Jong-Il Kim, Daejeon (KR); Yong Hee Kim, Sejong-si (KR); Myoung-Hwa Lim, Gyeonggi-do (KR); Min Soo Kim, Gangwon-do (KR); Dae-Chul Ha, Sejong-si (KR)

(73) Assignee: Korea United Pharm, Inc. (KR)

( * ) Notice: Subject to any disclaimer, the term of this patent is extended or adjusted under 35 U.S.C. 154(b) by 2 days.

(21) Appl. No.: 14/776,386

(22) PCT Filed: Mar. 14, 2014

(86) PCT No.: PCT/KR2014/002189
§ 371 (c)(1),
(2) Date: Sep. 14, 2015

(87) PCT Pub. No.: WO2014/142616
PCT Pub. Date: Sep. 18, 2014

(65) Prior Publication Data
US 2016/0030436 A1 Feb. 4, 2016

(30) Foreign Application Priority Data
Mar. 15, 2013 (KR) .................. 10-2013-0027945

(51) Int. Cl.
| | |
|---|---|
| A61K 31/5375 | (2006.01) |
| A61K 9/20 | (2006.01) |
| A61K 47/38 | (2006.01) |
| A61K 9/24 | (2006.01) |
| A61K 9/00 | (2006.01) |

(52) U.S. Cl.
CPC ........ *A61K 31/5375* (2013.01); *A61K 9/0053* (2013.01); *A61K 9/209* (2013.01); *A61K 9/2054* (2013.01); *A61K 47/38* (2013.01)

(58) Field of Classification Search
CPC .. A61K 31/5375; A61K 9/2054; A61K 47/38; A61K 9/209; A61K 9/0053
See application file for complete search history.

(56) References Cited

U.S. PATENT DOCUMENTS

| 5,009,895 A | 4/1991 | Lui | |
|---|---|---|---|
| 2007/0148230 A1* | 6/2007 | Fujiwara | A61K 9/0056 424/464 |
| 2011/0217374 A1 | 9/2011 | Oh et al. | |
| 2012/0135991 A1* | 5/2012 | Fujiwara | A61K 9/0056 514/237.8 |
| 2013/0022676 A1* | 1/2013 | Mullen | A61K 9/282 424/465 |
| 2013/0022677 A1* | 1/2013 | Mullen | A61K 9/2013 424/465 |

FOREIGN PATENT DOCUMENTS

| JP | H0753364 A | 2/1995 | |
|---|---|---|---|
| JP | 2010155854 A | 7/2010 | |
| KR | 10-2011-0055448 A | 5/2011 | |
| KR | 10-2011-0103113 A | 9/2011 | |
| KR | 20110103113 A * | 9/2011 | ........... A61K 9/1652 |
| KR | 10-2011-0113413 | 10/2011 | |
| KR | 10-2012-0083276 | 7/2012 | |
| KR | 10-2012-0094882 | 8/2012 | |
| WO | 9725065 A1 | 7/1997 | |

(Continued)

OTHER PUBLICATIONS

Rogers, T.L. "Hypromellose" in Handbook of Pharmaceutical Excipients. Pharmaceutical Press and American Pharmacists Association 2009 (6th Edition) 326-329.*
Hapgood, K.P., and S. Obara. "Hydroxypropyl Cellulose, Low-substituted" in Handbook of Pharmaceutical Excipients. Pharmaceutical Press and American Pharmacists Association 2009 (6th Edition) 322-324.*
Kim, Hye Jin, et al. "Formulation optimization of solid dispersion of mosapride hydrochloride." Archives of pharmacal research 34.9 (2011): 1467-1475.*

(Continued)

Primary Examiner — Bethany P Barham
Assistant Examiner — Peter Anthopolos
(74) Attorney, Agent, or Firm — Lerner, David, Littenberg, Krumholz & Mentlik, LLP (57) ABSTRACT

The formulation for oral administration of the present invention containing Mosapride or its salt is a double layer formulation consisting of a fast-release layer for rapid release of a drug and a sustained-release layer for slow release in order to simultaneously satisfy the rapid exhibition of pharmacological activities and sustained maintenance of pharmacological activities for 24 hours, wherein the high-viscosity hydroxypropyl methylcellulose (HPMC) and the low-viscosity HPMC are used in mixture such that the content of a high viscosity HPMC as a controlled-release matrix within the sustained-release layer has a higher content, thereby capable of controlling the dissolution rate in the regions having different pH values within the gastrointestinal tract and/or the retention time in the gastrointestinal tract. Additionally, the formulation of the present invention is a small-sized preparation with a total weight of 200 mg or less, preferably from 150 mg to 160 mg, thus capable of improving drug compliance of patients.

9 Claims, 5 Drawing Sheets (56) References Cited

FOREIGN PATENT DOCUMENTS

| WO | WO 03011256 A1 * | 2/2003 | ........... A61K 9/2018 |
|---|---|---|---|
| WO | 2011111818 A1 | 9/2011 | |
| WO | 2011126327 A3 | 2/2012 | |

OTHER PUBLICATIONS

International Search Report for Application No. PCT/KR2014/002189 dated Jun. 27, 2014.
Extended Search Report from European Application No. 14764801.8, dated Aug. 3, 2016.
Examination Report from the Taiwan Intellectual Property Office for Application No. 103131513 dated Jan. 25, 2016.

* cited by examiner

MOSAPRIDE SUSTAINED-RELEASE FORMULATION PROVIDING PHARMACOLOGICAL AND CLINICAL EFFECTS WITH ONCE-DAILY ADMINISTRATION

CROSS-REFERENCE TO RELATED APPLICATION

This application is a national phase entry under 35 U.S.C. § 371 of International Application No. PCT/KR/2014/002189, filed Mar. 14, 2014, which claims priority to Korean Patent Application No. 10-2013-0027945, filed on Mar. 15, 2013, the disclosures of which are incorporated herein by reference.

BACKGROUND OF THE INVENTION

1. Field of the Invention

The present invention relates generally to a sustained-release formulation for once-daily oral administration containing Mosapride with a total weight of 200 mg or less.

2. Description of the Related Art

As is well known in the art, 4-amino-5-chloro-2-ethoxy-N-{[4-(4-fluorobenzyl)-2-morpholinyl]methyl}benzamide (Mosapride) is a compound having a structure represented by Chemical Formula 1 below. Mosapride and its physiologically acceptable salts are selective serotonin 5-hydroxytryptamine 4 (hereinafter, '5-HT4') receptor agonists which selectively promote only the serotonin 5-HT4 receptors present in Plexus entercus, thus facilitating acetylcholine release from the nerve endings and also facilitating the movement of the digestive tract by constricting the smooth muscle of the digestive tract by the released acetylcholine, and thus serving as an effective drug for treating diabetic gastropathy, dyspepsia, gastritis, and gastroesophageal reflux disease. Mosapride is a safe drug free of the risks of arrhythmia and sudden cardiac death occurring in cisapride due to extension of QT intervals, dopamine-2 (D-2) receptor antagonistic action, central nervous system (CNS) adverse effects (extrapyramidal symptoms), and hyperprolactinemia (lactation, gynecomastia).

[Chemical Formula 1]

Mosapride, when orally administered, can be more than 93% absorbed in the digestive tract. Mosapride is distributed in the liver, small intestine, kidney, and adrenal glands at a concentration at least 10 times higher than that in blood plasma, distributed at high concentrations in the lungs, submaxillary gland, pancreas, hypophysis, thyroid gland, spleen, etc., and at a low concentration in eyeballs at about half the concentration in blood. Mosapride exhibits a fast drug effect by reaching its highest concentration in blood within from 0.5 hour to 1.4 hour when administered orally.

Due to the short half-life of Mosapride in the range of from 1.3 to 2 hours, Mosapride rapidly disappears once it is absorbed into a body, and thus it should be administered a few times because of its short duration of drug effect. Mosapride has been developed in tablets and is currently available on the market. Tablets containing 5 mg of Mosapride are recommended to be taken three times daily. Accordingly, it is necessary to improve the compliance of patients with the recommended use by reducing the number of administrations required, and also to maintain the drug effect by maintaining its concentration in blood.

Conventional sustained-release tablets have a disadvantage in that they require a long time for the drugs to reach an effective concentration in blood at the initial stage. Additionally, a fast exhibition of pharmacological activities of a given drug after its oral administration makes it difficult to maintain the effective pharmacological activities of the drug for 24 hours.

SUMMARY OF THE INVENTION

Accordingly, the present invention has been made keeping in mind the above problems occurring in the prior art, and an objective of the present invention is to provide a sustained-release formulation for once-daily oral administration containing Mosapride with a total weight of 200 mg or less, preferably from 150 mg to 160 mg, capable of maintaining an effective pharmacological effect for 24 hours while exhibiting rapid pharmacological activities upon its oral administration.

In order to accomplish the above objective, the present invention provides a sustained-release formulation for once-daily oral administration containing Mosapride or its salt as an active ingredient, wherein the formulation comprises:

a fast-release layer comprising the active ingredient, a filler, a disintegrating agent, and an additive; and a sustained-release layer comprising the active ingredient, a filler, a disintegrating agent, a controlled-release matrix, and an additive;

wherein the formulation has a gastrointestinal retention time of from 18 hours to 24 hours, releases from 20% to 50% of Mosapride or its salt in the stomach and from 50% to 80% of Mosapride or its salt in the intestinal tract during its transit through the gastrointestinal tract, wherein the formulation complies with the dissolution profile described below when the dissolution profile is measured according to the second method of the of dissolution test (paddle method) of the Korean Pharmacopoeia at 37° C. in dissolution media of pH 4.0, 6.8, 1.2 and water, a) the active ingredients contained in the formulation are released in the range of from 25% to 45% in 1 hour, from 60% to 80% in 8 hours, and at least 85% in 24 hours in the dissolution media of pH 4.0, 1.2 and water; and b) the active ingredients contained in the formulation are released 45% or less in 16 hours in the dissolution medium of pH 6.8;

wherein the sustained-release layer is prepared by mixing the high-viscosity hydroxypropyl methylcellulose (HPMC) having a viscosity of from 80,000 cps to 120,000 cps and the low-viscosity HPMC having a viscosity of 2,000 cps to 20,000 cps at a weight ratio in the range of from 10:1 to 1:1 as a controlled-release matrix.

The present invention is described in further detail below.

A drug is released in a dosage form while passing through the gastrointestinal tract, and finally dissolved and absorbed. For the absorption of a drug, it should first be released into the body fluid and dissolved in the region for absorption. For example, a drug in a tablet or capsule dosage form administered orally can be absorbed only after the molecules of the drug are released and dissolved in the gastrointestinal tract. Additionally, regarding once-daily drugs for administration, Mosapride or its salt with short half-lives are preferred to be released, dissolved, and then absorbed over a period of 20 hours or longer while being retained within the gastrointestinal tract for over 20 hours. The retention time of the drugs in the gastrointestinal tract can be controlled by means of the types of the components and/or composition ratio of a given formulation to be used.

Meanwhile, the stomach has a pH between 1 and 3, duodenum between 5 and 7, ascending colon between 7 and 8, and a jejunum has a pH of 6.5. If all drug components are released within 16 hours in various organs within the gastrointestinal tract after oral administration, Mosapride and its salt, due to their short half-life of from 1.3 to 2 hours, rapidly disappear once they are absorbed, and due to their short duration of drug effect, cannot maintain a 24-hour drug effect.

Examples of the Mosapride-containing formulations for oral administration of the present invention include a fast-release layer containing Mosapride or its salt (e.g., citrate), a filler, a disintegrating agent, an additive (e.g., a binder) and a sustained-release layer containing Mosapride or its salt, a filler, a disintegrating agent, controlled-release matrix, and an additive (e.g., a binder). The Mosapride-containing formulations for oral administration of the present invention may be in the form of a double layered tablet or a multiple-layered tablet, and may selectively include a lubricant.

The formulations of the present invention are prepared in a small size with a total weight of 200 mg or less, preferably in the range of from 150 mg to 160 mg, and thus they can be easily swallowed, thereby providing convenience for internal use medicine, and compliance and being cost-effective.

Meanwhile, the formulation for oral administration of the present invention containing Mosapride or its salt is characterized in that, in manufacturing a double layer formulation consisting of a fast-release layer for rapid release of a drug and a sustained-release layer for slow release in order to simultaneously satisfy the rapid exhibition of pharmacological activities and sustained maintenance of pharmacological activities for 24 hours, the weight ratio between the high-viscosity HPMC and the low low-viscosity HPMC are controlled while being mixed as a controlled-release matrix within the sustained-release layer, and thereby is capable of controlling the dissolution rate in the regions having different pH values within the gastrointestinal tract and/or the retention time in the gastrointestinal tract.

Figure 9:
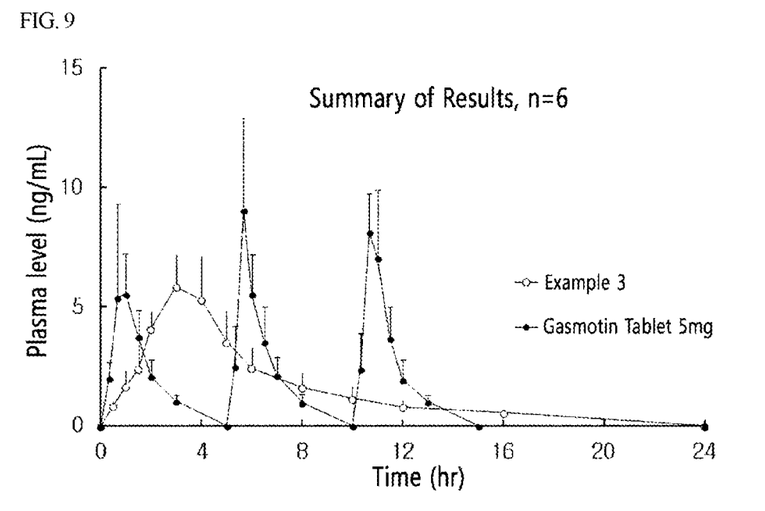
FIG. 9 is a graph illustrating the results of pre-clinical tests performed in Experimental Example 3.
Figure 10:
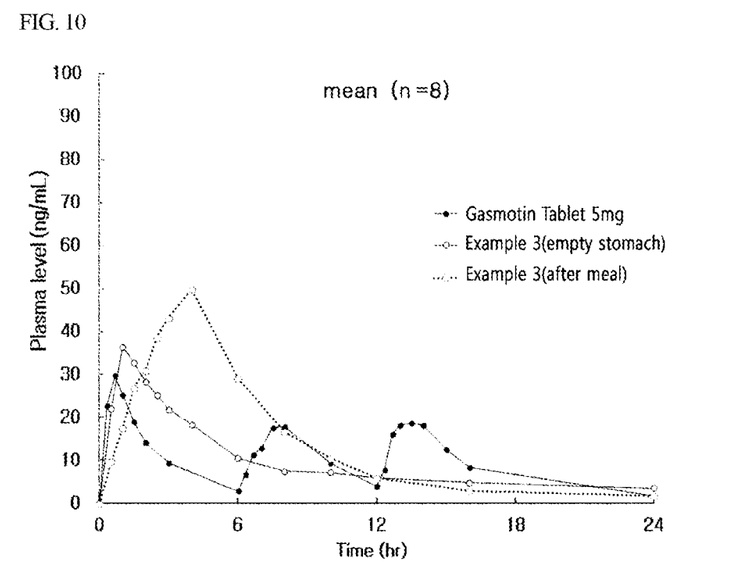
FIG. 10 is a graph illustrating the results of clinical tests performed in Experimental Example 4.

The inventors of the present invention, through experiments on dissolution rate at pH 4, discovered that the use of only a low-viscosity HPMC as a sustained-release matrix completely (100%) released Mosapride or its salt before 6 hours of passage, whereas the use of only a high-viscosity HPMC as a sustained-release matrix did not release Mosapride or its salt by 100% even after 24 hours of passage. Based on this result, the inventors of the present invention mixed the high-viscosity HPMC and the low-viscosity HPMC at a specific ratio to control the retention time and dissolution rate after reaching the small intestine as well as the retention time and dissolution rate before reaching the small intestine so that Mosapride or its salt can be released in small intestine and/or large intestine having a pH of 6.8, thereby succeeding in manufacturing a sustained-release formulation for once-daily oral administration capable of maintaining effective pharmacological activities for 24 hours (FIGS. 9 and 10).

In particular, the maintenance of the effective pharmacological activities for 24 hours was made possible because Mosapride or its salt can be released to the extent of 45% or less for 16 hours, preferably for 24 hours.

Surprisingly, the inventors of the present invention have discovered that when the high-viscosity HPMC and the low-viscosity HPMC were used together as a controlled-release matrix for Mosapride or its salt in the sustained-release layer, the dissolution rate at pH 4 reached 100% within 24 hours while the dissolution rate was drastically lowered at pH 6.8. Accordingly, by lowering the dissolution rate in duodenum after the drug passed the stomach or subsequently in the digestive tract, the drug was released in the gastric tract even 16 hours after the oral administration, and thus was capable of exhibiting pharmacological effect for around between 20 to 24 hours.

Accordingly, the sustained-release formulation for oral administration containing Mosapride of the present invention, by controlling the mixed ratio between the high-viscosity HPMC and the low-viscosity HPMC, preferably during its passage of gastrointestinal tract, can release from 20% to 50% of Mosapride or its salt in the stomach when passing through the gastrointestinal tract, and release from 50% to 80% of Mosapride or its salt in the gastric tract.

The viscosity of the high-viscosity HPMC is in the range of from 80,000 cps to 120,000 cps, and preferably is 100,000 cps. The viscosity of the low-viscosity HPMC is in the range of from 2,000 cps to 20,000 cps. In an embodiment, the low-viscosity HPMC used was 4,000 cps. In an embodiment of the present invention, the weight ratio between the high-viscosity HPMC and the low-viscosity HPMC may be from 10:1 to 1:1, preferably from 2.6:1 to 1:1.

HPMC, as a matrix for sustained-release, is a polymer for controlled-release, and has a relatively longer time for release compared to the conventional polymers for controlled-release such as methyl cellulose and polyvinyl acetate, and enables a relatively constant control of dissolution rate. The viscosity of HPMC can be controlled easily, but if a low-viscosity HPMC is used, it requires a greater amount of HPMC than when a high-viscosity HPMC be used, thus necessitating a larger size of tablets, thereby increasing production costs thereof and also reducing convenience in taking the tablets for internal use medicine due to the increased tablet size. However, the high-viscosity HPMC with a viscosity of 120,000 cps or higher is difficult to evenly mix with Mosapride citrate, a pharmacological active ingredient compared to the low-viscosity HPMC. The uneven mixture between the polymer for controlled-release and a pharmacologically active ingredient can cause an irregular dissolution rate, and therefore, low-viscosity HPMCs have been mainly used in the conventional art, even with the increase in the tablet weight.

To solve the above problem, in an embodiment of the present invention, the high-viscosity and the low-viscosity HPMC were mixed at a weight ratio of from 10:1 to 1:1, and then added with a specific ratio of povidone as a binder, microcrystalline cellulose as an excipient, lactose, low substituted hydroxypropylcellulose (hereinafter, L-HPC) as a disintegrating agent, thereby resolving the shortcomings of the high-viscosity HPMC and achieving an even mixture. Additionally, by reducing the variable factors that may occur during the scale-up of tablets, the change in dissolution rate due to the size of granules and tableting pressure has been almost eliminated, and also resolved the challenging issue of the establishment of reproducibility present in poly(methyl methacrylate)-based Eudragit® PL-PO (Ammonio Methacrylate Copolymer Type A), a sustained-release agent, caused by the change in dissolution rate due to the size of granules and tableting pressure.

Meanwhile, by mixing a greater amount of the high-viscosity HPMC to be used (weight basis) than the amount of the low-viscosity HPMC, the problem of rapid dissolution occurring when the amount of the low-viscosity HPMC exceeds the amount of the high-viscosity HPMC was resolved, and thereby manufacturing a sustained-release formulation for once-daily oral administration was possible.

Preferably, HPMC has a physical form with excellent dispersion and constant particle grindability for the same viscosity.

HPMC is added in the amount of from 5 wt % to 20 wt % relative to the total weight of a given formulation, preferably from 8 wt % to 16 wt %. When HPMC is added at less than 5 wt %, this results in rapid dissolution, whereas when HPMC is added more than 20 wt % it fails to show a constant dissolution of a given formulation.

Mosapride, the active ingredient of the present invention, is a serotonin receptor agonist capable of promoting the acetylcholine release from nerve endings by selectively acting on the serotonin (5-HT) receptors on the cholinergic neurons in the digestive tract, and facilitating the movement of the smooth muscle of the digestive tract by the released acetylcholine, thereby mediating strong movement of digestive tract and gastric emptying. Mosapride citrate is a type of Mosapride, and the two are pharmacologically the same. Mosapride citrate has a higher water solubility and higher melting point than Mosapride and thus can be more easily manufactured and purified.

The sustained-release tablet containing Mosapride citrate of the present invention is a specially designed formulation capable of a slow release of active ingredients contained in the formulation by controlling the dissolution rate of a given drug enabled by employing a matrix for sustained-release while having the same biological activities compared to those of other formulations in the conventional art. The sustained-release tablet containing Mosapride citrate of the present invention enables a once-daily oral administration of Mosapride citrate for patients having conventional gastrointestinal motility disorders instead of three-times daily oral administration, rapidly reaches effective therapeutic concentration in blood, and continuously maintains the effective therapeutic concentration in blood, thereby improving the therapeutic effects therefrom and also improving convenience for patients and compliance with drug administration requirements by simplifying the dose therapies.

Mosapride or its salt, as pharmacological active ingredients, are preferably contained in the amount of from 10 wt % to 20 wt % relative to the total weight of a given formulation. When the Mosapride or its salt is contained at less than 10 wt % it results in the reduction of pharmacological effect, whereas when it is contained at greater than 20 wt % it may cause adverse effects such as soft feces, diarthea, thirst, etc. When manufactured into a sustained-release tablet, the weight of the active ingredient per one tablet for once-daily oral administration is preferably about in the amount of from 10 mg to 20 mg.

A disintegrating agent serves to improve the dissolution rate of Mosapride or its salt by absorbing moisture and promoting disintegration of formulations. Non-limiting examples of the disintegrating agent to be used in the fast-release layer and the sustained-release layer of the present invention may include croscarmellose sodium, sodium starch glycolate, microcrystalline cellulose, crospovidone (cross-linked povidone) and other commercially useful polyvinyl pyrrolidone (PVP, povidone), L-HPC, alginic acid, powdered cellulose, starch, sodium alginate, and a mixture thereof. Preferably, the disintegrating agent is L-HPC or crospovidone. The disintegrating agent may be further added via a pharmaceutically acceptable method by adding it into a solid formulation for oral administration, and a secondary disintegrating agent may be additionally used for a faster dissolution of the formulation. Preferably, the disintegrating agent is used in the amount of from 10 wt % to 30 wt % relative to the total weight of the formulation, more preferably, from 20 wt % to 30 wt %.

Non-limiting examples of the excipient to be used in the fast-release layer and the sustained-release layer of the present invention may independently include lactose, mannitol, glucose, sorbitol, dextrin, sucrose, and a mixture thereof. Lactose serves to improve the ease of taking the tablet, facilitate a water-soluble channel when it is co-present with HPMC in a dissolution medium, and maintain the shape of tablets. Additionally, when lactose is mixed with high-viscosity HPMC it helps to form a uniform mixture between Mosapride citrate and HPMC. Preferably, lactose is added in the amount of from 15 wt % to 30 wt % relative to the total weight of a given formulation. When lactose is used at less than 15 wt % it is difficult to form a uniform mixture between high-viscosity HPMC and its salt, and also the mixture attaches to the punch of a tableting machine, thus causing a sticking phenomenon. In contrast, when lactose is used more than 30 wt % it has a problem to increase the total weight of the formulation. Alternatively, other excipients, for example, from 10 wt % to 30 wt % of mannitol relative to the total weight of the formulation, from 10 wt % to 30 wt % of sorbitol relative to the total weight of the formulation, from 20 wt % to 40 wt % of glucose relative to the total weight of the formulation, from 20 wt % to 30 wt % of dextrin relative to the total weight of the formulation, or from 20 wt % to 40 wt % of sucrose may be used instead of lactose.

In an embodiment of the present invention, a binder, as a water-soluble polymer which can be dissolved in an organic solvent and improve the binding force of a given formulation, may be used in the fast-release layer and the sustained-release layer. Non-limiting examples of the binder to be used may include polyvinyl pyrrolidone (povidone K-30 having a conventional name of povidone and a molecular weight of 30 is used). Preferably, the binder is added in the amount of from 3 wt % to 10 wt %. When the binder is added at less than 3 wt % the binding force of the formulation becomes weak thus making the tableting process difficult, whereas when the binder is added at more than 10 wt % it becomes difficult to control the dissolution rate of a given drug.

Non-limiting examples of the lubricant to be used in the fast-release layer and the sustained-release layer of the present invention may independently include light anhydrous silicic acid, silicon dioxide, talc, stearic acid, magnesium stearate or a mixture thereof. The lubricant improves the mobility of power/granule materials thereby increasing the tableting machine's fillability into a die, a lower part of the tableting machine, while reducing the friction between the power/granule materials themselves and between a punch, an upper part of the tabletting machine, and the die, thereby making the compression and release of tablets easy.

Preferably, the lubricant is used in the amount of from 0.5 wt % to 5 wt %. When the lubricant is added at less than 0.5 wt % it makes the tabletting process difficult, whereas when the lubricant is added at more than 5 wt % it affects the dissolution feature of tablets due to the coating phenomenon of lubricant granules.

The composition of the formulation containing Mosapride of the present invention may include 10 wt % to 15 wt % of Mosapride or its salt as a pharmacologically active ingredient, 5 wt % to 10 wt % of high-viscosity HPMC, 5 wt % to 10 wt % of low-viscosity HPMC, 15 wt % to 30 wt % of lactose, 3 wt % to 10 wt % of povidone, and 0.5 wt % to 5 wt % of lubricants relative to the total weight of the formulation. The composition of the formulation containing Mosapride of the present invention is a composition for a double-layered sustained-release tablet consisting of a fast-release layer and a sustained-release layer.

In an embodiment, the formulation containing Mosapride for oral administration of the present invention may be manufactured by respectively mixing, kneading, and granulating the fast-release layer and the sustained-release layer followed by tabletting. First, in the sustained-release layer are mixed 13 wt % to 15 wt % of Mosapride or its salt as a pharmacologically active ingredient, 15 wt % to 30 wt % of lactose, 25 wt % to 30 wt % of HPMC, and 15 wt % to 30 wt % of L-HPC, relative to the total weight of the sustained-release layer, kneaded and granulated by adding 3 wt % to 10 wt % of povidone as a binder solution, dissolved in advance in an adequate amount of ethanol, and then dried in a cabinet dryer at between 50° C. and 60° C. to 2% or less of loss on drying (LOD) and then controlled a size of the particles. Then, the resultant is mixed with an adequate amount of lubricants to manufacture the sustained-release layer. In addition, in the fast-release layer are mixed 6 wt % to 8 wt % of Mosapride or its salt, 15 wt % to 30 wt % of lactose, 25 wt % to 40 wt % of L-HPC, relative to the total weight of the fast-release layer, kneaded and granulated by adding 3 wt % to 10 wt % of povidone as a binder solution, dissolved in advance in an adequate amount of ethanol, and then dried in a cabinet dryer at between 50° C. and 60° C. to 2% or less of loss on drying (LOD) and then controlled a size of the particles. Then, the resultant is mixed with an adequate amount of lubricants to manufacture the fast-release layer. A multi-layer tablet may be manufactured by conducting a primary tabletting of the sustained-release layer among the mixtures manufactured above, followed by a secondary tabletting on top of the sustained-release layer by filling with the fast-release layer. Here, the tabletting of the fast-release layer is not necessarily performed after the tabletting of the sustained-release layer. That is, the tabletting of the fast-release layer may be performed first and then the granules of the sustained-release layer may be filled in to be tabletted thereafter. Additionally, the fast-release layer and the sustained-release layer may be filled in sequentially in this order or in reverse order and may be tabletted once.

The formulation containing Mosapride for oral administration of the present invention may be a pellet-type tablet or a multi-layer tablet manufactured by mixing the fast-release layer and the sustained-release layer.

Accordingly, for the formulation containing Mosapride for oral administration of the present invention, by an in vivo experiment conducted on a healthy subject, the highest Mosapride citrate concentration in blood (Cmax ng/ml) may be in the range of from 40 to 50 ng/mL, and the area under the blood concentration-time curve ($AUC_t$ h*ng/mL) may be in the range of from 200 to 240 h*ng/mL, and the time required for reaching the highest concentration in blood (Tmax, h) may be between 1.0 and 4.0 hours.

The double-layer tablet of the present invention consisting of the fast-release layer and the sustained-release layer containing the same active ingredients, upon conducting a dissolution test at pH 4.0 using 900 mL of dissolution medium according to the paddle method with 50 revolutions per minute (the Korean Pharmacopoeia $10^{th}$ revision, the second method of dissolution test), showed the respective dissolution rates for 1 hour, 8 hours, and 24 hours from the onset of the dissolution test as from 25% to 45%, from 60% to 80%, and equal to or higher than 85%. When the dissolution test was performed in water, pH 1.2, pH 4.0, and pH 6.8 dissolution media, both the sustained-release formulation containing Mosapride citrate of the present invention and those according to the conventional technology showed different dissolution features depending on pH conditions.

In order to predict the drug effects of the formulation in the human body by comparing the dissolution features and pharmacological kinetics, the pharmacological activities were confirmed in a beagle dog using a formulation having the composition shown in the Examples. As a result, it was confirmed that the pharmacological kinetics of Mosapride citrate varied according to the in vitro dissolution characteristics, and that an appropriate dissolution feature in an in vitro experiment enables a desirable pharmacological activities in in vivo environments.

Furthermore, upon examining the in vivo pharmacological kinetics of Mosapride citrate in the human body using the formulation, in which the above pharmacological kinetics were confirmed, the rapid pharmacological activities aimed at by the present invention were confirmed to be exhibited, and also a mosapride citrate concentration in blood higher than the minimum effective mosapride citrate concentration in blood was confirmed to be maintained for 24 hours.

Advantageous Effects

The double-layer tablet for oral administration consisting of the fast-release layer and the sustained-release layer manufactured according to the present invention can control the dissolution rate of a drug by means of a pharmaceutically acceptable matrix for sustained-release, can rapidly reach the effective therapeutic concentration in blood upon administration thereby immediately showing improved effects on gastrointestinal motility disorder despite having the same biological activities as those of the conventional technology, and also can maintain the active ingredients and effective activity metabolites in the blood plasma at a constant concentration for a considerable period of time. Accordingly, the tablet of the present invention with a reduced number of required doses and a smaller size compared to those of conventional formulations can provide patients with an improved convenience regarding its administration, thus increasing drug adaptability and patient compliance.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

A better understanding of the present invention may be obtained through the following examples which are set forth to illustrate, but are not to be construed as limiting the scope of the present invention.

Examples 1-7 and Comparative Examples 1-6

Preparation of a Fast-Release Layer:

According to the components described in Tables 1 and 2, Mosapride citrate, microcrystalline cellulose, lactose hydrate, and L-HPC were mixed, and added to povidone K-30 solution dissolved in advance in ethanol, and then kneaded, granulated and dried in a cabinet dryer at between 50° C. and 60° C. for from 30 to 40 minutes (to 2% or less of LOD). The resultant was controlled a size of the particles and the remaining lubricants were mixed.

Preparation of a Sustained-Release Layer:

According to the components described in Tables 1 and 2, Mosapride citrate, microcrystalline cellulose, lactose hydrate, low-viscosity HPMC (4000 cps, HPMC 2910), high-viscosity HPMC (100,000 cps, HPMC 2208), and L-HPC were mixed, and added to povidone K-30 solution dissolved in advance in ethanol, and then kneaded, granulated and dried in a cabinet dryer at between 50° C. and 60° C. for from 30 to 40 minutes (to 2% or less of LOD). The resultant was controlled a size of the particles and the remaining lubricants were mixed.

Preparation of a Double Layer Tablet:

A double layer tablet was tableted using a mixture of the a fast-release layer and the sustained-release layer prepared above, and then film-coated with OPADRYOY-C-7000A (a commercial name for a coating matrix manufactured by Colorcone, Co., Ltd.) by a conventional method, and thereby a sustained-release tablet containing 15 mg of Mosapride citrate as Mosapride per tablet was prepared.

TABLE 1

| Category | Components | Compounds | Comp. Ex. 1 | Ex. 1 | Ex. 2 | Ex. 3 | Ex. 4 | Ex. 5 | Ex. 6 | Ex. 7 |
|---|---|---|---|---|---|---|---|---|---|---|
| Fast-Release Layer | active ingredient | Mosapride citrate | 5.29 | 5.29 | 5.29 | 5.29 | 5.29 | 5.29 | 5.29 | 5.29 |
| | excipient | microcrystalline cellulose | 21.00 | 21.00 | 21.00 | 21.00 | 21.00 | 21.00 | 21.00 | 21.00 |
| | excipient | lactose hydrate | 18.76 | 18.76 | 18.76 | 18.76 | 18.76 | 18.76 | 18.76 | 18.76 |
| | disintegrating agent | L-HPC | 24.00 | 24.00 | 24.00 | 24.00 | 24.00 | 24.00 | 24.00 | 24.00 |
| | binder | povidone K-30 | 5.00 | 5.00 | 5.00 | 5.00 | 5.00 | 5.00 | 5.00 | 5.00 |
| | lubricant | light anhydrous silicic acid | 0.33 | 0.33 | 0.33 | 0.33 | 0.33 | 0.33 | 0.33 | 0.33 |
| | lubricant | magnesium stearate | 0.62 | 0.62 | 0.62 | 0.62 | 0.62 | 0.62 | 0.62 | 0.62 |
| | Total (mg/tablet) | | 75.00 | 75.00 | 75.00 | 75.00 | 75.00 | 75.00 | 75.00 | 75.00 |
| Sustained-Release Layer | active ingredient | Mosapride citrate | — | 10.58 | 10.58 | 10.58 | 10.58 | 10.58 | 10.58 | 10.58 |
| | excipient | microcrystalline cellulose | — | 13.00 | 13.00 | 13.00 | 13.00 | 13.00 | 13.00 | 13.00 |
| | excipient | lactose hydrate | — | 9.49 | 9.49 | 9.49 | 9.49 | 9.49 | 9.49 | 9.49 |
| | sustained-release matrix | low-viscosity HPMC (HPMC 2910) | — | 2.00 | 6.00 | 8.00 | 10.00 | 14.00 | 16.00 | 20.00 |
| | sustained-release matrix | high-viscosity HPMC (HPMC 2208) | — | 20.00 | 16.00 | 14.00 | 12.00 | 8.00 | 6.00 | 2.00 |
| | binder | povidone K-30 | — | 5.00 | 5.00 | 5.00 | 5.00 | 5.00 | 5.00 | 5.00 |
| | disintegrating agent | L-HPC | — | 14.00 | 14.00 | 14.00 | 14.00 | 14.00 | 14.00 | 14.00 |
| | lubricant | light anhydrous silicic acid | — | 0.31 | 0.31 | 0.31 | 0.31 | 0.31 | 0.31 | 0.31 |

TABLE 1-continued

| Category | Components | Compounds | Comp. Ex. 1 | Ex. 1 | Ex. 2 | Ex. 3 | Ex. 4 | Ex. 5 | Ex. 6 | Ex. 7 |
|---|---|---|---|---|---|---|---|---|---|---|
| | lubricant | magnesium stearate | — | 0.62 | 0.62 | 0.62 | 0.62 | 0.62 | 0.62 | 0.62 |
| | coating agent | OPADRY OY-C-7000A | — | 5.00 | 5.00 | 5.00 | 5.00 | 5.00 | 5.00 | 5.00 |
| Total (mg/tablet) | | | 75.00 | 155.00 | 155.00 | 155.00 | 155.00 | 155.00 | 155.00 | 155.00 |

TABLE 2

| Category | Components | Compounds | Comp. Ex. 2 | Comp. Ex. 3 | Comp. Ex. 4 | Comp. Ex. 5 | Comp. Ex. 6 |
|---|---|---|---|---|---|---|---|
| Fast-Release Layer | active ingredient | Mosapride citrate | 5.29 | 5.29 | 5.29 | 5.29 | 5.29 |
| | excipient | microcrystalline cellulose | 21.00 | 21.00 | 21.00 | 21.00 | 21.00 |
| | excipient | lactose hydrate | 18.76 | 18.76 | 18.76 | 18.76 | 18.76 |
| | disintegrating agent | L-HPC | 24.00 | 24.00 | 24.00 | 24.00 | 24.00 |
| | binder | povidone K-30 | 5.00 | 5.00 | 5.00 | 5.00 | 5.00 |
| | lubricant | light anhydrous silicic acid | 0.33 | 0.33 | 0.33 | 0.33 | 0.33 |
| | lubricant | magnesium stearate | 0.62 | 0.62 | 0.62 | 0.62 | 0.62 |
| | Total (mg/tablet) | | 75.00 | 75.00 | 75.00 | 75.00 | 75.00 |
| Sustained Release Layer | active ingredient | Mosapride citrate | 10.58 | 10.58 | 10.58 | 10.58 | 10.58 |
| | excipient | microcrystalline cellulose | 20.00 | 15.00 | 10.00 | 10.00 | 5.00 |
| | excipient | lactose hydrate | 9.49 | 9.49 | 9.49 | 9.49 | 9.49 |
| | sustained-release matrix | low-viscosity HPMC (HPMC 2910) | 15.00 | 20.00 | 25.00 | — | — |
| | sustained-release matrix | high-viscosity HPMC (HPMC 2208) | — | — | — | 25.00 | 30.00 |
| | binder | povidone K-30 | 5.00 | 5.00 | 5.00 | 5.00 | 5.00 |
| | disintegrating agent | L-HPC | 14.00 | 14.00 | 14.00 | 14.00 | 14.00 |
| | lubricant | light anhydrous silicic acid | 0.31 | 0.31 | 0.31 | 0.31 | 0.31 |
| | lubricant | magnesium stearate | 0.62 | 0.62 | 0.62 | 0.62 | 0.62 |
| | coating agent | OPADRY OY-C-7000A | 5.00 | 5.00 | 5.00 | 5.00 | 5.00 |
| Total (mg/tablet) | | | 155.00 | 155.00 | 155.00 | 155.00 | 155.00 |

Experimental Example 1

Figure 1:
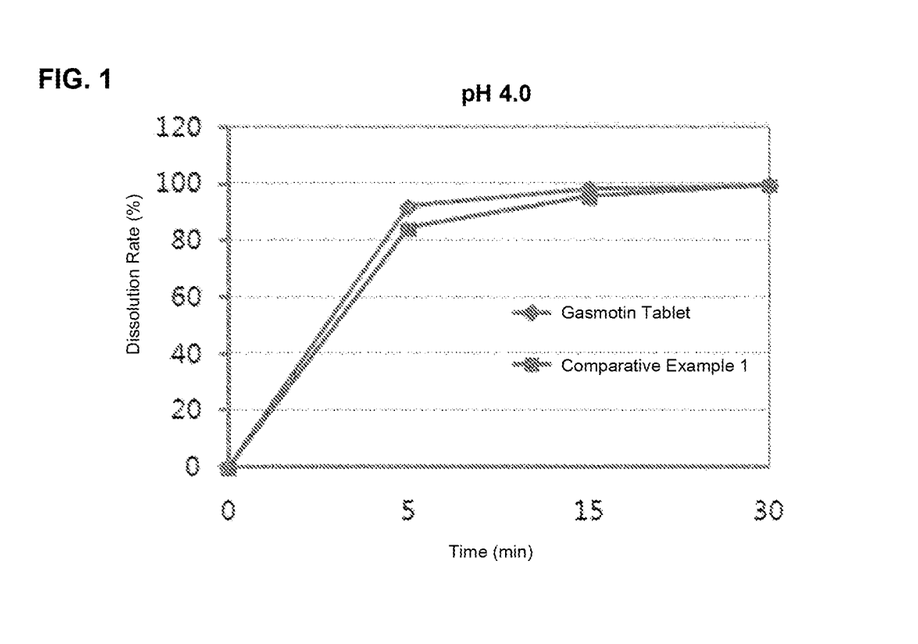
FIG. 1 is a graph illustrating the dissolution rate in a dissolution medium of pH 4.0 of Gasmotin tablet 5 mg, a formulation and control drug prepared in Comparative Example 1.

Dissolution features of Gasmotin tablets 5 mg (Mosapride 5 mg, Daewoong Co., Ltd.) available in the commercial market and the tablets consisting of only a fast-release layer prepared in Comparative Example 1 were compared using their dissolution media of pH 4.0. Here, an in vitro dissolution test was performed according to the second method of general test with paddle revolutions of 50 rpm/min (the Korean Pharmacopoeia), and the result is shown in FIG. 1. In the tablets consisting of only the fast-release layer of Comparative Example 1, 100% of the drug was released within 30 minutes, similar to the dissolution rate of the Gasmotin tablets.

Meanwhile, in order to examine the changes in dissolution features of formulations according to the presence or absence of addition of high-viscosity or low-viscosity controlled-release matrix (sustained-release matrix) to the sustained-release layer, and the amount thereof (wt %), Mosapride citrate tablets of Comparative Examples 2-6 were manufactured according to the components in Table 2. Here, the tablet weight was adjusted with microcrystalline cellulose excipient, i.e., a filler. The dissolution features of tablets of Comparative Examples 2-6 were observed at pH 4.0, and the results are shown in FIGS. 2 and 3.

Consideration

Figure 2:
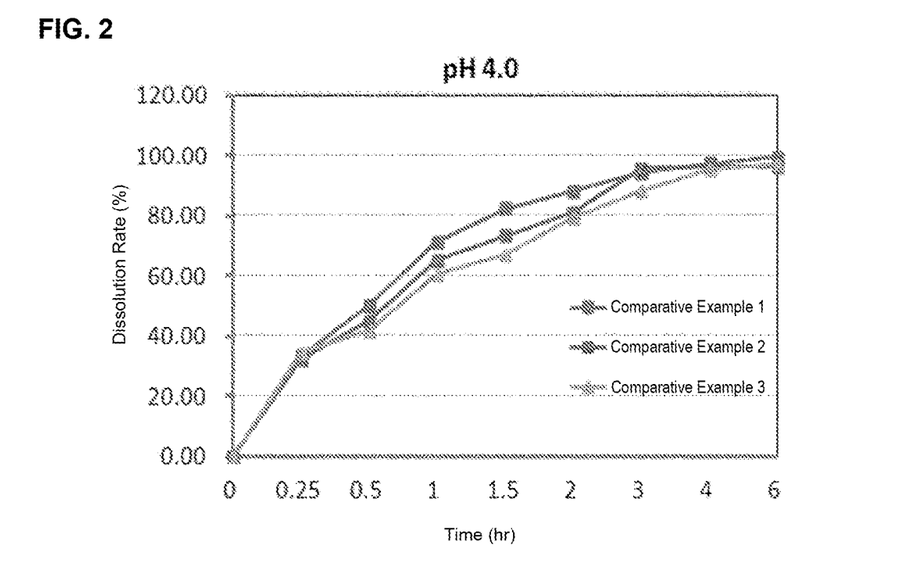
FIG. 2 is a graph illustrating the dissolution rate in a dissolution medium of pH 4.0 of formulations prepared in Comparative Examples 2 to 4.
Figure 3:
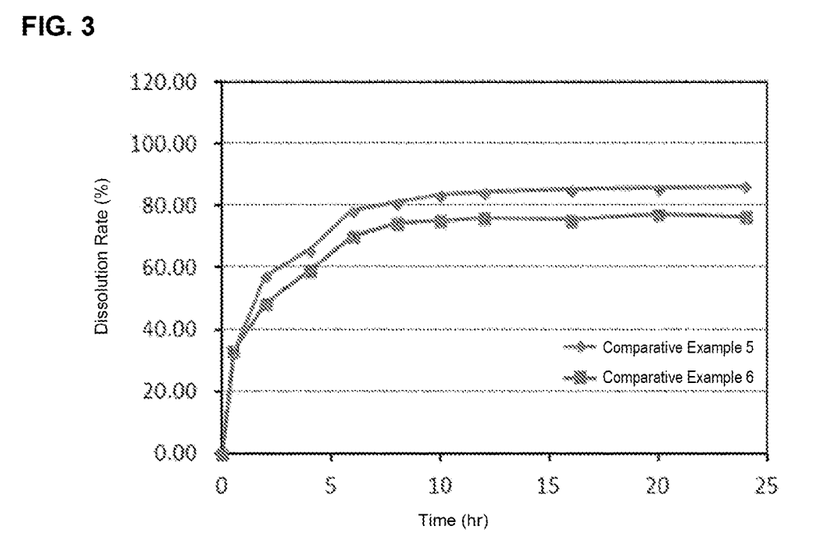
FIG. 3 is a graph illustrating the dissolution rate in a dissolution medium of pH 4.0 of formulations prepared in Comparative Examples 5 and 6.

Regarding the dissolution rate, the tablets manufactured using only the sustained-release matrix with low-viscosity as in Comparative Examples 2-4 showed a 100% release of the drugs before 6 hours, thus failing to exhibit sustained release (FIG. 2). Meanwhile, in the tablets manufactured using only the sustained-release matrix with high-viscosity (HPMC 2208) as in Comparative Examples 5 and 6, the drugs were not released by 100% even after 24 hours, thus showing a long sustained-release (FIG. 3).

Figure 4:
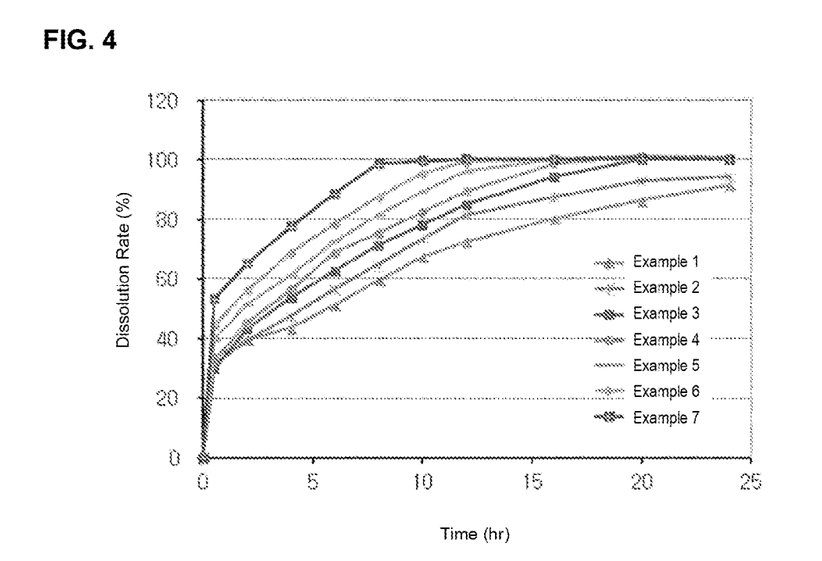
FIG. 4 is a graph illustrating the dissolution rate in a dissolution medium of pH 4.0 of formulations prepared in Examples 1 to 7.
Figure 5:
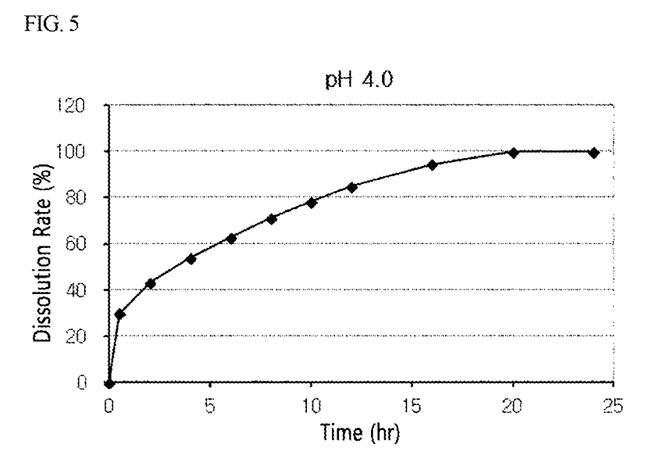
FIG. 5 is a graph illustrating the dissolution rate in a dissolution medium of pH 4.0 of formulations prepared in Example 3.
Figure 6:
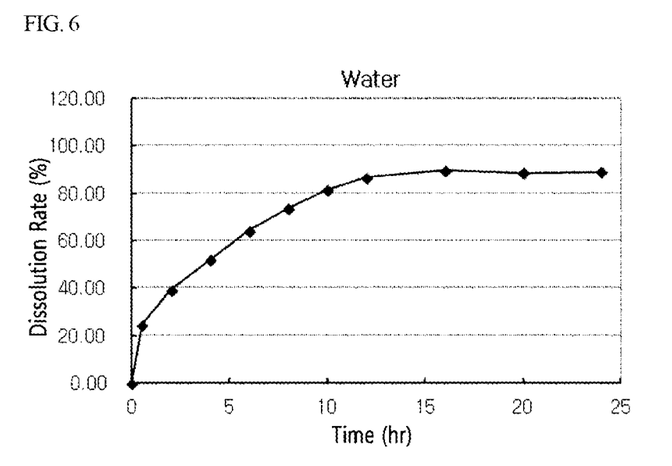
FIG. 6 is a graph illustrating the dissolution rate in water as a dissolution medium of formulations prepared in Example 3.
Figure 7:
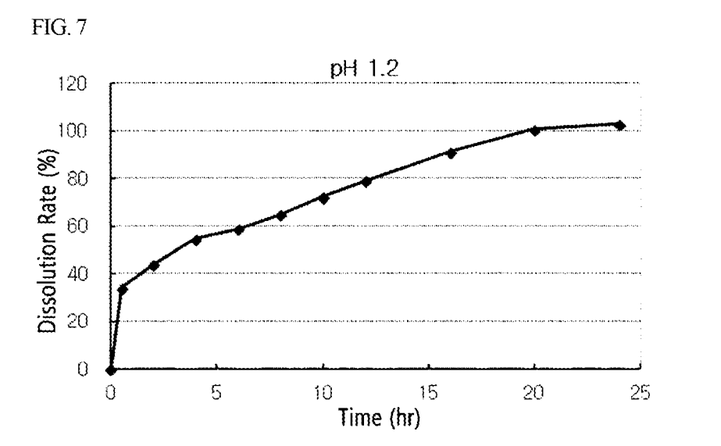
FIG. 7 is a graph illustrating the dissolution rate in a dissolution medium of pH 1.2 of formulations prepared in Example 3.
Figure 8:
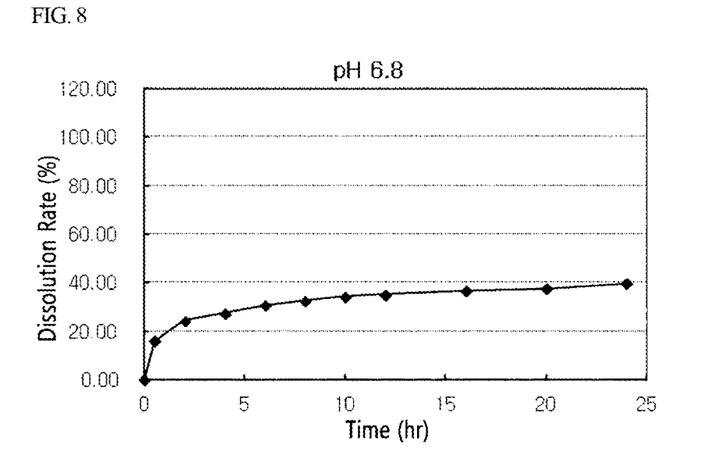
FIG. 8 is a graph illustrating the dissolution rate in a dissolution medium of pH 6.8 of formulations prepared in Example 3.

FIG. 4 shows dissolution rates of tablets manufactured by mixing the low-viscosity sustained-release matrix and the high-viscosity sustained-release matrix at a specific ratio as in Examples 1-7. The tablets manufactured in Examples 5-7 showed a faster release at the initial stage with an increase in the amount of the low-viscosity sustained-release matrix and the time required for a 100% release of the drug became shorter. Therefore, the tablets were not expected to meet the once-daily administration effect.

Examples 1 and 4 illustrate tablets having a higher content of the high-viscosity sustained-release matrix than the low-viscosity sustained-release matrix, and the drugs in the tablets were released by 60% or less after 4 hours. In the tablets in Example 3, the drugs were released by about 30% at the early dissolution stage, being similar to the drug content of the fast-release layer, and showed a constant sustained-release around 20 hours from the onset, and the drugs were completely released at about between 20 and 24 hours from the onset. Accordingly, the tablets of Example 3 are expected to have a desirable minimum and maximum effective concentration in the blood, and are thus desirable as sustained-release formulations for once-daily administration.

Experimental Example 2

The sustained-release formulation of Example 3 was chosen as the final formulation to undergo clinical tests, and the amounts and weight ratios of the raw materials of the sustained-release formulations of Example 3 are shown in Table 3 below.

Example 3 illustrates double layer tablets consisting of a fast-release layer and a sustained-release layer, wherein the sustained-release layer contains a suitable amount of high-viscosity HPMC and low-viscosity HPMC as sustained-release matrices. Therefore, most of the drugs in the tablets are not released until they reach duodenum having a pH of 4, and a considerable amount of the drugs can be released in the small intestine and/or large intestine with a pH of 6.8, and it is thus considered as a candidate group with the highest potential for 24 hour sustained release of a given drug. Additionally, having the pH 4.0 condition exhibiting a relatively constant and stable dissolution rate set as a standard dissolution, the test standards and methods were established as the dissolution rate 1 hour after the onset is from 25% to 45%, 8 hours after the onset is from 60% to 80%, and 24 hours after the onset is 85% or higher.

Various Tests of Dissolution Rates of Dissolution Media at Various pH Conditions Subject: sustained-release formulation containing Mosapride citrate prepared in Example 4

Dissolution test solution: disintegration test of the Korean Pharmacopoeia (pH 1.2, 4.0, 6.8, and water) 900 mL, Test temperature: 37±0.5

Dissolution method: the second method of dissolution test (paddle method) in General test of Korean Pharmacopoeia, 50 rpm/min.

The dissolution features of sustained-release formulations containing Mosapride citrate according to pH change were examined by performing an in vitro test, and the results are shown in Table 4 and FIGS. 5-8.

TABLE 3

| Category | Components | Compounds | Weight per tablet (mg) | Ratio relative to total weight (%) | Ratio according to fast-release layer/sustained-release layer (%) |
| --- | --- | --- | --- | --- | --- |
| Fast-release layer | active ingredient | Mosapride citrate | 5.29 | 3.53 | 7.05 |
| | excipient | microcrystalline cellulose | 21.00 | 14.00 | 28.00 |
| | excipient | lactose hydrate | 18.76 | 12.51 | 25.01 |
| | disintegrating agent | L-HPC | 24.00 | 16.00 | 32.00 |
| | binder | povidone K-30 | 5.00 | 3.33 | 6.67 |
| | lubricant | light anhydrous silicic acid | 0.33 | 0.22 | 0.44 |
| | lubricant | magnesium stearate | 0.62 | 0.41 | 0.83 |
| | | Total (mg/tablet) | 75.00 | — | 100.45 (≈100) |
| Sustained-release layer | active ingredient | Mosapride citrate | 10.58 | 7.05 | 14.11 |
| | excipient | microciystalline cellulose | 13.00 | 8.67 | 17.33 |
| | excipient | lactose hydrate | 9.49 | 6.33 | 12.65 |
| | sustained-release matrix | low-viscosity HPMC (HPMC 2910) | 8.00 | 5.33 | 10.67 |
| | sustained-release matrix | high-viscosity HPMC (HPMC 2208) | 14.00 | 9.33 | 18.67 |
| | binder | povidone K-30 | 5.00 | 3.33 | 6.67 |
| | a disintegrating agent | L-HPC | 14.00 | 9.33 | 18.67 |
| | lubricant | light anhydrous silicic acid | 0.31 | 0.21 | 0.41 |
| | lubricant | magnesium stearate | 0.62 | 0.41 | 0.83 |
| | coating agent | OPADRY OY-C-7000A | 5.00 | 100 | 100.01 |
| | | Total (mg/tablet) | 155.00 | | (≈100) |

TABLE 4

| Test Solution | Average Dissolution Rate (%) | | | | | | | | | |
|---|---|---|---|---|---|---|---|---|---|---|
| | 0.5 hr | 2 hr | 4 hr | 6 hr | 8 hr | 10 hr | 12 hr | 16 hr | 20 hr | 24 hr |
| pH 4.0 | 29.88 | 43.36 | 53.86 | 62.87 | 71.38 | 78.20 | 84.97 | 94.47 | 100.20 | 100.10 |
| water | 24.61 | 39.13 | 51.92 | 64.34 | 73.77 | 81.44 | 86.67 | 89.85 | 88.62 | 88.99 |
| pH 1.2 | 34.04 | 43.75 | 54.66 | 58.75 | 64.91 | 72.31 | 79.04 | 91.35 | 100.65 | 103.01 |
| pH 6.8 | 16.02 | 24.49 | 27.55 | 30.70 | 32.61 | 34.46 | 35.23 | 36.79 | 37.56 | 39.68 |

The results showed that the dissolution rate was constant and continuous in pH 1.2 and water conditions and thus the bioavailability of the Mosapride citrate as an active ingredient was expected to be maintained for 24 hours. Additionally, the pH 6.8 condition showed a low dissolution rate due to the physicochemical characteristics of Mosapride citrate, and the influences of sustained-release matrices and excipients constituted therein.

Experimental Example 3

The pharmacokinetic (PK) characteristics of Mosapride citrate was examined via a pre-clinical test using the sustained-release formulation of Example 3 which had its dissolution features confirmed at various in vitro pH conditions.

The test method includes administering one tablet of each of a test material (a sustained-release table containing Mosapride citrate) and Gasmotin 5 mg in market to a beagle dog (a male, n=6) via oral administration, respectively, collecting blood samples at a predetermined time, separating blood plasma from the collected blood, and measuring the concentration of Mosapride and its salt in the blood plasma of the beagle dog.

As pharmacokinetic parameters, the area under the blood concentration-time curve (AUCt) from the onset of administration to the time point t quantitating the final concentration in blood, the area under the blood concentration-time curve (AUC∞) from the onset of administration to and unlimited time, maximum concentration in blood (Cmax), time required for reaching the highest concentration in blood (tmax), and half-life (t½) in blood loss were calculated via BA Calc 2007 program. For AUC∞ and Cmax, those divided by dose amounts were used and indicated as AUCi/doseC and max/dose, respectively, and the average ratio between AUCt and AUCi was indicated as AUCt/AUCi. The significance on materials was confirmed via student's t-test at 95% confidence, and the results are shown in Table 5 below and FIG. 9.

Upon examining the pk characteristics of Mosapride in a beagle dog with one tablet of Gasmotin 5 mg as a control drug and the sustained-release tablet of Mosapride citrate prepared in Example 3, it was confirmed that Cmax increased at the initial stage, and the time required for reaching maximum concentration in blood (Tmax) of the Mosapride was delayed due to the sustained-release matrix, thus having a similar feature to the in vitro dissolution feature. The above result was expected to correspond to the objective of the solution to the technical problem presented by the present invention, and on this basis, the optimum effect was confirmed in the clinical test, demonstrating the final goal of the present invention.

Experimental Example 4

In order to evaluate the pharmacodynamic equivalence of the formulations of the present invention, randomized assignment, open-label, single-dose, 3-treatment groups, 3-period Williams design Study phase I clinical tests were performed on healthy male subjects for comparative evaluation of pharmacokinetic characteristics and the influence of foods during oral administration of a Mosapride citrate sustained-release formulation and a Mosapride fast-release formulation (Gasmotin 5 mg, Daewoong Co., Ltd) with a composition of Example 3. The subjects were 48 healthy male volunteers aged between 20 and 55 selected according to the standards of selection and elimination of clinical test procedures. The detailed test conditions are shown in Table 6 below, and the results are shown in Table 7 and FIG. 10.

TABLE 5

| Category | PK parameters | G1 | G2 | G3 | G4 | G5 | G6 | mean | Standard Deviation |
|---|---|---|---|---|---|---|---|---|---|
| Control drug (Gasmotin tablet) | AUC (last) | 24.66 | 41.80 | 30.55 | 19.24 | 40.38 | 29.55 | 31.036 | 8.78 |
| | AUC (inf) | 25.33 | 43.16 | 31.58 | 20.24 | 41.81 | 31.44 | 32.26 | 8.98 |
| | Cmax | 7.480 | 15.62 | 12.89 | 5.783 | 11.14 | 9.406 | 10.38 | 3.60 |
| | Tmax | 5.67 | 5.67 | 0.67 | 10.67 | 11 | 5.67 | 6.55 | 3.84 |
| Test Material (Sustained-release formulation of Ex. 3) | AUC (last) | 37.94 | 48.16 | 30.11 | 24.34 | 22.95 | 21.66 | 30.86 | 10.39 |
| | AUC (inf) | 40.91 | 50.70 | 33.35 | 27.22 | 25.80 | 23.67 | 33.61 | 10.45 |
| | Cmax | 7.12 | 7.98 | 6.40 | 5.23 | 5.37 | 4.45 | 6.09 | 1.32 |
| | Tmax | 3 | 4 | 4 | 3 | 3 | 3 | 3.33 | 0.52 |

Test/Ref (%) - AUC (last): 99.4, AUC (inf): 104.2, Cmax: 58.7

TABLE 6

| | |
|---|---|
| Drugs for Clinical Tests | Test drug: UI05MSP015CT, once-daily oral administration (Mosapride citrate 15 mg, Korea United Pharm. Inc.) Formulation type - tablet, dose - 15 mg/1T Control drug: Gasmotin tablet, 3 times daily (every 6 hours) oral administration (Mosapride citrate 5 mg, Daewoong Co., Ltd.) formulation type - film-coated tablet, dose - 5 mg/1T |
| Designing Tests | Single-dose, Randomized, Open-label, 3-Treatment, 3-Period Williamsdesign Study Randomized assignment to 6 sequential groups consisting of a combination of Control drug (empty stomach), Test drug (empty stomach), and Test drug (after meal), and application of each treatment group per each period Withdrawal Period: More than 7 days from the first day of administration Blood collection Time: Control drug: before administration per each period (0 h) (the first administration after blood collection), 0.33, 0.67, 1, 1.5, 2, 3, 6 (the second administration after blood collection), 6.33, 6.67, 7, 7.5, 8, 10, 12 (the third administration after blood collection), 12.33, 12.67, 13, 13.5, 14, 15, 16 and 24 h (a total of 23 times) Test drug: before administration per each period (0 h)(the first administration after blood collection), 0.5, 1, 1.5, 2, 2.5, 3, 4, 6, 8, 10, 12, 16, 24 h (a total of 14 times) Method of drug analysis: LC-MS/MS |
| No. of Subjects | Control drug (Reference, R) treatment group: Gasmotin tablet (Mosapride citrate 5 mg) one tablet, 3 times daily (every 6 hours) administration on an empty stomach (a total of 15 mg) Test drug (Test/fasted, T) treatment group: UI05MSP015CT (Mosapride citrate 15 mg) one tablet, once-daily administration on an empty stomach (a total of 15 mg) After meal test drug (Test/fed, IP) test group: UI05MSP015CT (Mosapride citrate 15 mg) one tablet, once-daily administration after meal (a total of 15 mg) |
| Statistical Analysis | Pharmacokinetic parameters are calculated after analyzing the concentration of a given drug, and determined as equivalent only when the difference between the primary evaluation item values of control drug (empty stomach) and test drug (empty stomach) for Cmax and AUCt as the primary evaluation items and the log-transformed mean values of the primary evaluation item values at 90% confidence is between log 0.8 and log 1.25. Additionally, pharmacokinetic parameters are calculated after analyzing the concentration of a given drug, and the effect of foods is evaluated by calculating the difference between log-transformed mean values of the primary evaluation item values of test drug (empty stomach) and test drug (after meal) at 90% confidence. |

The results of pharmacodynamic equivalence tests on sustained-release of Mosapride citrate formulation of Example 3 and Gasmotin tablet 5 mg performed under the test conditions described in Table 6 above were shown to have pharmacodynamic equivalence between the two formulations at 90% confidence, as shown in Table 7 and FIG. 10.

TABLE 7

| | Mean ± SD | | |
|---|---|---|---|
| pharmacokinetic parameters | Gasmotin tablet 5 mg (empty stomach) | Sustained-release formulation of Example 4 (empty stomach) | Sustained-release formulation of Example 4 (after meal) |
| $C_{max}$ (ng/mL) | 37.5 (±15.0) | 41.1 (±17.9) | 46.5 (±14.9) |
| $AUC_{24}$ (h * ng/mL) | 201.0 (±58.7) | 207.6 (±111.7) | 238.7 (±60.8) |
| AUC (h * ng/mL) | 311.5 (±177.8) | 227.1 (±123.7) | 245.1 (±62.9) |
| Tmax (h) | 6.2 (±6.3) | 1.0 (±0.5) | 3.8 (±1.2) |
| $t_{1/2}$ (h) | 12.8 (±5.7) | 5.2 (±1.7) | 3.6 (±0.9) |

What is claimed is:

1. A sustained-release formulation for once-daily oral administration containing Mosapride or its salt as an active ingredient,
   wherein the formulation comprises:
   a fast-release layer comprising the active ingredient, a filler, a disintegrating agent, and a binder; and
   a sustained-release layer comprising the active ingredient, a filler, a low substituted hydroxypropylcellulose (L-HPC), a controlled-release matrix, and a binder;
   wherein the formulation has a gastrointestinal retention time of from 18 hours to 24 hours, releases from 20% to 50% of Mosapride or its salt in the stomach and from 50% to 80% of Mosapride or its salt in the intestinal tract during its transit through the gastrointestinal tract,
   wherein the formulation complies with the dissolution profile described below when the dissolution profile is measured according to the second method of the of dissolution test (paddle method) of the Korean Pharmacopoeia at 37° C. in dissolution media of pH 4.0, 6.8, 1.2 and water,
   a) the active ingredients contained in the formulation are released in the range of from 25% to 45% in 1 hour, from 60% to 80% in 8 hours, and at least 85% in 24 hours in the dissolution media of pH 4.0, 1.2 and water; and b) the active ingredients contained in the formulation are released 45% or less in 16 hours in the dissolution medium of pH 6.8;

wherein the controlled-release matrix is a mixture of high-viscosity hydroxypropyl methylcellulose (HPMC) having a viscosity of from 80,000 cps to 120,000 cps and low-viscosity HPMC having a viscosity of 2,000 cps to 20,000 cps, wherein weight ratio between the high-viscosity HPMC and low-viscosity HPMC is in the range of from 2.6:1 to 1:1, and the total amount of the high-viscosity HPMC and the low-viscosity HPMC is from 5 to 20 wt % relative to the total weight of the formulation.

2. The sustained-release formulation of claim 1, wherein the total weight of the formulation is equal to or less than 200 mg.

3. The sustained-release formulation of claim 1, wherein the total weight of the formulation is in the range of from 150 mg to 160 mg.

4. The sustained-release formulation of claim 1, wherein the amount of the active ingredient in the fast-release layer is from 6 wt % to 8 wt % relative to the total weight of the fast-release layer, and the amount of the active ingredient in the sustained-release layer is from 13 wt % to 15 wt % relative to the total weight of the sustained-release layer.

5. The sustained-release formulation of claim 1, wherein each of the fast-release layer and the sustained-release layer further comprises a lubricant.

6. A sustained-release formulation for once-daily oral administration containing Mosapride or its salt as an active ingredient, wherein the formulation comprises:

a fast-release layer comprising the active ingredient, a lactose hydrate, a low substituted hydroxypropylcellulose (L-HPC), and a polyvinyl pyrrolidone; and a sustained-release layer comprising the active ingredient, a controlled-release matrix, a lactose hydrate, a L-HPC, and a polyvinyl pyrrolidone;

wherein the formulation has a gastrointestinal retention time of from 18 hours to 24 hours, releases from 20% to 50% of Mosapride or its salt in the stomach and from 50% to 80% of Mosapride or its salt in the intestinal tract during its transit through the gastrointestinal tract, wherein the formulation complies with the dissolution profile described below when the dissolution profile is measured according to the second method of the of dissolution test (paddle method) of the Korean Pharmacopoeia at 37° C. in dissolution media of pH 4.0, 6.8, 1.2 and water, a) the active ingredients contained in the formulation are released in the range of from 25% to 45% in 1 hour, from 60% to 80% in 8 hours, and at least 85% in 24 hours in the dissolution media of pH 4.0, 1.2 and water; and b) the active ingredients contained in the formulation are released 45% or less in 16 hours in the dissolution medium of pH 6.8;

wherein the controlled-release matrix is a mixture of high-viscosity hydroxypropyl methylcellulose (HPMC) having a viscosity of from 80,000 cps to 120,000 cps and low-viscosity HPMC having a viscosity of 2,000 cps to 20,000 cps, wherein weight ratio between the high-viscosity HPMC and low-viscosity HPMC is in the range of from 2.6:1 to 1:1; and the total amount of the high-viscosity HPMC and the low-viscosity HPMC is from 5 to 20 wt % relative to the total amount of the formulation.

7. The sustained-release formulation of claim 6, wherein the sustained-release layer comprises 13 to 15 wt % of Mosapride citrate;

25 to 35 wt % of HPMC with 4,000 cps of viscosity and HPMC with 100,000 cps of viscosity;

15 to 30 wt % of lactose hydrate;

15 to 30 wt % of low substituted hydroxypropylcellulose (L-HPC), and 3 to 10 wt % of polyvinyl pyrrolidone relative to the total weight of the sustained-release layer.

8. The sustained-release formulation of claim 6, wherein the amount of the active ingredient in the fast-release layer is from 6 wt % to 8 wt % relative to the total weight of the fast-release layer, and the amount of the active ingredient in the sustained-release layer is from 13 wt % to 15 wt % relative to the total weight of the sustained-release layer.

9. The sustained-release formulation of claim 6, wherein each of the fast-release layer and the sustained-release layer further comprises a lubricant.

\* \* \* \* \*